US009329123B2

(12) United States Patent
Harb

(10) Patent No.: US 9,329,123 B2
(45) Date of Patent: May 3, 2016

(54) MULTIPLEXED SPECTROSCOPIC ABSORBANCE FROM CRDS WAVE FORMS

(71) Applicant: NewSouth Innovations Pty Limited, Sydney (AU)

(72) Inventor: Charles Charbel Harb, Bungendore (AU)

(73) Assignee: NewSouth Innovations Pty Limited, Sydney, New South Wales (AU)

( * ) Notice: Subject to any disclaimer, the term of this patent is extended or adjusted under 35 U.S.C. 154(b) by 0 days.

(21) Appl. No.: 14/424,850

(22) PCT Filed: Aug. 6, 2013

(86) PCT No.: PCT/AU2013/000866
§ 371 (c)(1),
(2) Date: Feb. 27, 2015

(87) PCT Pub. No.: WO2014/032078
PCT Pub. Date: Mar. 6, 2014

(65) Prior Publication Data
US 2015/0226666 A1    Aug. 13, 2015

(30) Foreign Application Priority Data

Aug. 30, 2012 (AU) ................................. 2012903768

(51) Int. Cl.
*G01N 21/39* (2006.01)
*G01J 3/42* (2006.01)
(Continued)

(52) U.S. Cl.
CPC ................. *G01N 21/39* (2013.01); *G01J 3/021* (2013.01); *G01J 3/10* (2013.01); *G01J 3/42* (2013.01);
(Continued)

(58) Field of Classification Search
USPC .................................................. 356/432–444
See application file for complete search history.

(56) References Cited

U.S. PATENT DOCUMENTS 5,912,740 A * 6/1999 Zare ........................... G01J 3/10
356/437
5,973,782 A * 10/1999 Bomse .................. G01J 3/4338
356/451

(Continued)

FOREIGN PATENT DOCUMENTS

WO        2012021943 A1    2/2012

OTHER PUBLICATIONS

International Search Report and Written Opinion for corresponding PCT Application No. PCT/AU2013/000866, dated Sep. 23, 2013 (5 pgs.).

(Continued)

*Primary Examiner* — Tri Ton
*Assistant Examiner* — Jarreas C Underwood
(74) *Attorney, Agent, or Firm* — Shumaker & Sieffert, P.A.

(57) ABSTRACT

Methods and optical detection systems (200, 300, 800, 900) for generating and processing a real-time time-domain cavity ringdown spectroscopy (CRDS) signal (831, 931) from an absorbing species in an optical detection system (200, 300, 800, 900) having an optical ringdown cavity (200, 300) are disclosed. The optical ringdown cavity (200, 300) is adapted for accepting a sample of an absorbing species. One or more modulated light signals (241,243,245,341) are generated using one or more light sources (240, 242, 244, 340). The light source(s) (240, 242, 244, 340) is pulsed at a specified pulse rate(s). The modulated light signal(s) (241,243,245, 341) is resonated using the optical ringdown cavity (200, 300) comprising a plurality of mirrors (220, 230), or sets of mirrors (320, 330), to produce the CRDS signal (831, 931). The reflectivity of the mirrors (220, 230), or sets of mirrors (320, 330), is dependent upon the pulse rate of the modulated light signals (241,243,245,341). Different beamlines (212, 214, 216, 312, 314, 316) are established by the modulated light signal(s) (241,243,245, 341) and the mirrors (220, 230, 320, 330) interacting with the absorbing species sample.

60 Claims, 10 Drawing Sheets

(51) Int. Cl.
    *H01S 3/08*           (2006.01)
    *G01N 21/3504*     (2014.01)
    *G01N 21/03*       (2006.01)
    *G01J 3/02*        (2006.01)
    *G01J 3/10*        (2006.01)
    *G01J 3/427*      (2006.01)
    *G01J 3/433*      (2006.01)
    *H01S 3/105*      (2006.01)

(52) U.S. Cl.
    CPC ............... *G01J 3/427* (2013.01); *G01J 3/433* (2013.01); *G01N 21/031* (2013.01); *G01N 21/3504* (2013.01); *G01J 2003/102* (2013.01); *G01N 2201/06113* (2013.01); *H01S 3/08063* (2013.01); *H01S 3/105* (2013.01)

(56) References Cited

U.S. PATENT DOCUMENTS

| | | | |
|---|---|---|---|
| 6,377,350 B1 * | 4/2002 | Paldus | G01J 3/10 356/454 |
| 7,106,763 B2 * | 9/2006 | Tan | G01N 21/39 372/33 |
| 7,113,286 B2 * | 9/2006 | Yan | G01J 3/42 356/436 |
| 7,768,647 B2 * | 8/2010 | Reeve | G01J 3/10 356/435 |
| 7,884,938 B2 * | 2/2011 | Cole | G01J 3/42 356/437 |

OTHER PUBLICATIONS

International Preliminary Report on Patentability for corresponding PCT Application No. PCT/AU2013/000866, dated Jun. 16, 2014 (25 pgs.).

* cited by examiner

MULTIPLEXED SPECTROSCOPIC ABSORBANCE FROM CRDS WAVE FORMS

RELATED APPLICATION

The present application is a national stage entry under 35 U.S.C. 371 of PCT Application No. PCT/AU2013/000866 filed on Aug. 6, 2013 in the name of NewSouth Innovations Pty Limited, which claims the benefit of, and is entitled to rely on, the earlier filing date of Australian Provisional Patent Application No. 2012903768 filed on Aug. 30, 2012 in the name of NewSouth Innovations Pty Limited. The entire contents of each of PCT Application No. PCT/AU2013/000866 and Australian Provisional Patent Application No. 2012903768 are incorporated herein by reference in its their entirety.

TECHNICAL FIELD

The present invention relates to a detection system for analysis of a signal and in particular to a harmonic detection system for generating and analysing CRDS signals.

The invention has been developed primarily for use as a harmonic detection scheme for analysing optical absorbance signals in real time and is described hereinafter with reference to this application. However, it will be appreciated that the invention is not limited to this particular field of use.

BACKGROUND

Any discussion of the background art throughout the specification should in no way be considered as an admission that such background art is prior art, nor that such background art is widely known or forms part of the common general knowledge in the field.

The detection of substances posing chemical, biological and explosives (CBE) threats has become critical in recent years, for example, for airport security. Many advances in instrumentation designed for trace detection have been made to locate illicit compounds. A significant hindrance has been the requirement to measure compounds of interest given their low concentrations. Hence, significant interest has developed in techniques enhancing the signal from a species of interest while simultaneously reducing sensitivity to contaminants.

For use in such an application, cavity ringdown spectroscopy (CRDS) analysis systems and methods for analysing an absorbance signal are disclosed in International (PCT) Patent Application Publication No. WO 2012/021943 (PCT/AU2011/001071) published on 23 February in the name of NewSouth Innovations Pty Limited et al. In one aspect, the system comprises: a modulator, a light source, an optical cavity, a detector, a mixer, a signal transformer, a determiner module, and an analyser module. The modulator generates a modulation signal. The light source is adapted to be modulated using the modulation signal. The optical cavity resonates modulated light from the light source and outputs an absorbance signal. The detector detects the absorbance signal and generates a time-dependent detected signal. The mixer multiplies the detected signal with the modulation signal to generate a mixed signal. The signal transformer transforms the mixed signal and generates a Fourier transformed time-decay signal. The determiner module determines the magnitude of each transformed time-decay signal at the fundamental frequency and at least one frequency other than the fundamental frequency to generate several frequency-dependent magnitude signals. The analyser module analyses the frequency-dependent magnitude signals to determine data representative of the absorbance signal. This is done to determine the absorbance of a sample fundamental frequency and at a frequency other than the fundamental frequency. The system is able to analyse data quickly and is insensitive to noise sources that occur at frequencies other than those in the modulated light signal.

SUMMARY

The following definitions are provided as general definitions and should in no way limit the scope of the present invention to those terms alone, but are set forth for a better understanding of the following description.

Unless defined otherwise, all technical and scientific terms used herein have the same meaning as commonly understood by those of ordinary skill in the art to which the invention belongs. For the purposes of the present invention, the following terms are defined below:

The articles "a" and "an" are used herein to refer to one or to more than one (i.e. to at least one) of the grammatical object of the article. By way of example, "an element" refers to one element or more than one element.

The term "about" is used herein to refer to quantities that vary by as much as 30%, preferably by as much as 20%, and more preferably by as much as 10% to a reference quantity.

Throughout this specification, unless the context requires otherwise, the words "comprise", "comprises" and "comprising" will be understood to imply the inclusion of a stated step or element or group of steps or elements, but not the exclusion of any other step or element or group of steps or elements.

The term "real time", for example "displaying real time data", refers to the display of the data without intentional delay, given the processing limitations of the system and the time required to accurately measure the data. Similarly, the phrase "analysing a signal in real time" refers to the analysis of a signal and presentation or output of data representative of the signal without intentional delay, given the processing limitations of the system and the time required to accurately analyse the signal and present the output of such analysis.

In accordance with an aspect of the invention, there is provided a method of generating and processing a real-time time-domain cavity ringdown spectroscopy (CRDS) signal from an absorbing species in an optical detection system having an optical ringdown cavity. The optical ringdown cavity is adapted for accepting a sample of an absorbing species. Modulated light signals are generated using a number of light sources having different wavelengths. The light sources are pulsed at specified pulse rates. The modulated light signals are resonated using the optical ringdown cavity comprising a plurality of mirrors to produce the CRDS signal. Each mirror has the same or substantially the same reflectivity. The selectivity of the mirrors is dependent upon the pulse rate of the modulated light signals. Different beamlines are established by the modulated light signals and the mirrors interacting with the absorbing species sample.

The method may further comprise: detecting the CRDS signal output by the optical ringdown cavity for the multiplexed modulated light signals; and estimating the cavity ringdown times $\tau$ and determining spectra for the absorbing species sample from the detected CRDS signal by mixing the detected CRDS signal dependent upon the wavelengths and the selected harmonics of the modulated light signals from the light sources.

In accordance with another aspect of the invention, there is provided a method of generating and processing a real-time time-domain cavity ringdown spectroscopy (CRDS) signal from an absorbing species in an optical detection system having an optical ringdown cavity. The optical ringdown cavity is adapted for accepting a sample of an absorbing species. A modulated light signal is generated using a light source. The light source is pulsed at a specified pulse rate. The modulated light signal is resonated using the optical ringdown cavity comprising a number of sets of mirrors to produce the CRDS signal. Each set of mirrors has the same or substantially the same reflectivity. The selectivity of the mirrors is dependent upon the pulse rate of the modulated light signal. Different beamlines are established by the modulated light signal and the mirrors interacting with the absorbing species sample.

The method may further comprise: detecting the CRDS signal output by the optical ringdown cavity for the multiplexed beamlines; and estimating the cavity ringdown times and determining spectra for the absorbing species sample from the detected CRDS signal by mixing the detected CRDS signal dependent the selected harmonics of the modulated light signal from the light source.

In accordance with still another aspect of the invention, there is provided a method of generating and processing a real-time time-domain cavity ringdown spectroscopy (CRDS) signal from an absorbing species in an optical detection system having an optical ringdown cavity. The optical ringdown cavity is adapted for accepting a sample of an absorbing species. Modulated light signals are generated using a number of light sources having different wavelengths. The light sources are pulsed at specified pulse rates. The modulated light signals are resonated using the optical ringdown cavity comprising a number of sets of mirrors to produce the CRDS signal. Each set of mirrors has the same or substantially the same reflectivity. The selectivity of the mirrors is dependent upon the pulse rates of the modulated light signals. Different beamlines are established by the modulated light signals and the mirrors interacting with the absorbing species sample.

The method may further comprise: detecting the CRDS signal output by the optical ringdown cavity for the multiplexed beamlines; and estimating the cavity ringdown times $\tau$ and determining spectra for the absorbing species sample from the detected CRDS signal by mixing the detected absorbance signal CRDS dependent upon the wavelengths and the selected harmonics of the modulated light signals from the light sources.

Different beamlines may be adjusted such that the reflectivities of input and output mirrors of the optical ringdown cavity are different for each beamline.

The estimating step may comprise calculating the power of selected harmonics using mixers and signal sources for the selected harmonics.

The spectra determining step may comprise plotting the ring-down rate R or the reciprocal of the ring-down decay constant $1/\tau$ versus the wavelength $\lambda$ of the incident light.

The method may further comprise identifying the absorbing species by comparing the determined spectra for the absorbing species sample with a library of predetermined spectra for known elements.

The multiplexed beamlines using mirrors with selected reflectivities and the use of matching pulse rate of the light sources allows the estimating and determining steps to be optimally processed.

The method may further comprise controlling dependent upon the detected CRDS signal the one or more light sources and/or the optical ringdown cavity.

In accordance with a further aspect of the invention, there is provided an optical detection system for generating and processing a real-time time-domain cavity ringdown spectroscopy (CRDS) signal from an absorbing species. The system comprises: a plurality of light sources and an optical ringdown cavity. The light sources have different wavelengths that generate modulated light signals. The light sources are pulsed at specified pulse rates. The optical ringdown cavity is adapted for accepting a sample of an absorbing species. The optical ringdown cavity comprises a plurality of mirrors configured to resonate the modulated light signals to produce the CRDS signal. Each mirror has the same or substantially the same reflectivity. The selectivity of the mirrors is dependent upon the pulse rate of the modulated light signals. Different beamlines are established by the modulated light signals and the mirrors interacting with the absorbing species sample.

The optical detection system may further comprise: a photodetector for detecting the CRDS signal output by the optical ringdown cavity for the multiplexed modulated light signals; and a module for estimating the cavity ringdown times T and a module for determining spectra for the absorbing species sample from the detected CRDS signal by mixing the detected CRDS signal dependent upon the wavelengths and the selected harmonics of the modulated light signals from the light sources.

In accordance with a further aspect of the invention, there is provided an optical detection system for generating and processing a real-time time-domain cavity ringdown spectroscopy (CRDS) signal from an absorbing species, the system comprising: a light source and an optical ringdown cavity. The light source generates a modulated light signal. The light source is pulsed at a specified pulse rate. The optical ringdown cavity is adapted for accepting a sample of an absorbing species. The optical ringdown cavity comprises a plurality of sets of mirrors configured to resonate the modulated light signal to produce the CRDS signal. Each set of mirrors has the same or substantially the same reflectivity. The selectivity of the mirrors is dependent upon the pulse rate of the modulated light signal. Different beamlines are established by the modulated light signal and the mirrors interacting with the absorbing species sample.

The optical detection system may further comprise: a photodetector for detecting the CRDS signal output by the optical ringdown cavity for the multiplexed beamlines; and a module for estimating the cavity ringdown times $\tau$ and a module for determining spectra for the absorbing species sample from the detected. CRDS signal by mixing the detected CRDS signal dependent the selected harmonics of the modulated light signal from the light source.

In accordance with yet another aspect of the invention, there is provided an optical detection system for generating and processing a real-time time-domain cavity ringdown spectroscopy (CRDS) signal from an absorbing species. The system comprises: a plurality of light sources and an optical ringdown cavity. The plurality of light sources have different wavelengths that generate modulated light signals. The light sources are pulsed at specified pulse rates. The optical ringdown cavity is adapted for accepting a sample of an absorbing species. The optical ringdown cavity comprises a plurality of sets of mirrors configured to resonate the modulated light signals to produce the CRDS signal. Each set of mirrors has the same or substantially the same reflectivity. The selectivity of the mirrors is dependent upon the pulse rates of the modulated light signals. Different beamlines are established by the modulated light signals and the mirrors interacting with the absorbing species sample.

The optical detection system may further comprise: a photodetector for detecting the CRDS signal output by the optical ringdown cavity for the multiplexed beamlines; and a module for estimating the cavity ringdown times τ and a module for determining spectra for the absorbing species sample from the detected CRDS signal by mixing the detected absorbance signal CRDS dependent upon the wavelengths and the selected harmonics of the modulated light signals from the light sources.

Regarding the foregoing aspects of the invention, the optical ringdown cavity may comprise a multipass cell adapted to be resonant. The resonant multipass cell has an input coupler and an output coupler positioned or located in a beampath and having a reflectivity that reflects light back upon itself inside a cavity of the multipass cell. The resonant multipass preferably comprises a Herriott Cell.

Various aspects of the optical detection systems may be implemented in accordance with the aspects of the methods described herein.

BRIEF DESCRIPTION OF DRAWINGS

Arrangements of the detection system are described hereinafter, by way of an example only, with reference to the accompanying drawings, in which.

DETAILED DESCRIPTION

Figure 1:
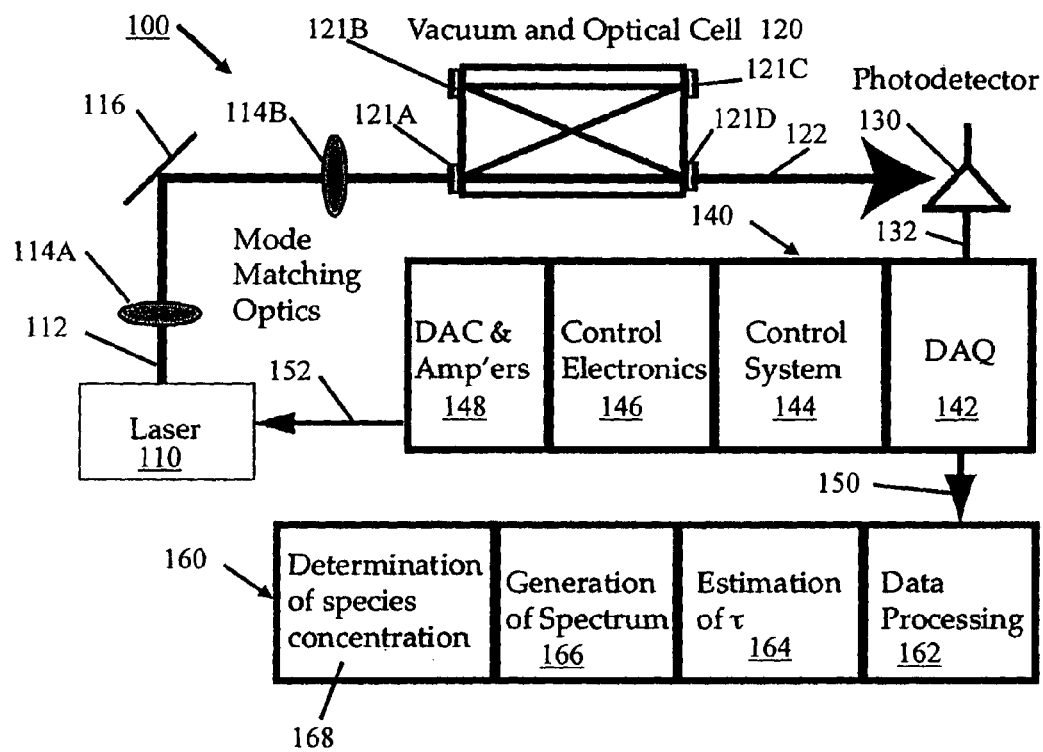
FIG. 1 is a block diagram illustrating a real-time laser-based spectrometer, with which embodiments of the invention may be practiced, with appropriate modification as described hereinafter with reference to the embodiments of the invention.

Methods and optical detection systems for generating and processing a real-time time-domain cavity ringdown spectroscopy (CRDS) signal from an absorbing species in an optical detection system having an optical ringdown cavity are disclosed hereinafter. The optical ringdown cavity is adapted for accepting a sample of an absorbing species. In the following description, numerous specific details, including particular pulse rates, pulse durations, absorbing species, and the like are set forth. However, from this disclosure, it will be apparent to those skilled in the art that modifications and/or substitutions may be made without departing from the scope and spirit of the invention. In other circumstances, specific details may be omitted so as not to obscure the invention.

With reference to the drawings, systems and methods for digital detection for analysis of time-decaying signals are disclosed herein. By way of example, optical absorbance signals are detected and analysed.

The embodiments of the invention provide an improved system of analysing absorbance signals relative to the system of International (PCT) Patent Application Publication No. WO 2012/021943. In particular, systems and methods are disclosed herein that are able to make real-time time-domain cavity ringdown spectroscopy (CRDS) measurements with one or more lasers and mirror combinations simultaneously by multiplexing signals. A method of generating and processing a real-time time-domain CRDS signal from an absorbing species in an optical detection system. Further, the systems and methods advantageously utilise the reflectivity of sets of mirrors and the pulse rate of light sources to multiplex beamlines for absorbance measurements. The systems and methods disclosed herein improve the dynamic range of such measurements by adjusting laser decay time using multiple reflectivity mirrors.

Cavity Ringdown Spectroscopy Generally

Any waveform may be represented by a weighted sum of sines and cosines. In electronic systems, the extent to which a sine wave of a given frequency contributes to an arbitrary waveform may be determined by using a mixer, which may be either analog or digital. The mixer accepts as inputs a signal waveform and a signal generated by a local oscillator, which is commonly either a sine function of known frequency f or a square wave signal. The DC component of the mixer output is a signal proportional to the extent to which a sine wave of frequency f contributes to the signal waveform. By scanning the local oscillator frequency, a complex signal in time can be decomposed into a frequency-domain spectrum analogous to that obtained by applying a Fourier-transform.

Using a sine wave as the local oscillator of a mixer, the contribution of only a single frequency component to a signal waveform is measured. If several frequencies are of interest, an alternative local oscillator may be used to simultaneously measure contributions of a set of sine waves having different frequencies. For example, a square wave of frequency f is composed of a set of sine waves whose frequencies are f, 3f, 5f, 7f, 9f, . . . . With a square wave as the local oscillator signal, the mixed signal obtained from the output of the mixer is therefore a measure of the combined contribution of sine waves at f, 3f, 5f, 7f, 9f, or higher harmonics to the signal waveform. In this way, a mixer can be used to determine the simultaneous contributions of a set of sine functions to a signal waveform. Therefore, by using an appropriate local oscillator signal waveform, the contribution of a set of sine waves to a complex waveform may be quickly determined. It should be noted that this detection scheme has the advantage of filtering out all noise sources except those sources that happen to occur at f, 3f, 5f, 7f, 9f, and higher harmonics.

Whilst not limited to the analysis of signals typically obtained from a locked cavity ring-down spectroscopic system, the signal analysis technique described herein is readily described with reference to a time-domain signal, for example for analysis of an interferogram (i.e. from an interferometer), or alternatively for analysis of signal degeneration in an optical communications system (e.g. for transport of optical modulated signals over a communications links such as in free-space or optical fibre).

In a cavity ringdown spectroscopy (CRDS) system, the sample (absorbing material) is placed in a high-finesse stable optical resonator or ringdown cavity (the terms may be used interchangeably hereinafter) having an input coupling mirror and an output-coupling mirror. Light admitted into the ring-down cavity through the input coupler circulates back and forth multiple times setting up standing waves having periodic spatial variations. Light exiting through the output coupler is proportional to the intra-cavity light intensity. After the input light source is terminated, the radiant energy stored in the ring-down cavity decreases in time (rings-down). For an empty cavity, the stored energy follows an exponential decay characterized by a ring-down rate that depends only on the reflectivity of the mirrors, the separation between the mirrors and the speed of light in the cavity. If a sample is placed in the resonator, the ring-down is accelerated; under suitable conditions, the intra-cavity energy decays almost perfectly exponentially.

In cavity ringdown spectroscopy (CRDS), the decay of light trapped in the high-finesse optical cavity is a direct measure of absorbance (also known as optical density) by gas-phase molecules within the cavity. Absorbance is measured by monitoring the ring-down decay constant, $\tau$, of a signal, I, which is decaying exponentially in time, t, described by:

$$I = O + A \cdot \exp[-t/\tau] \quad (1)$$

where O is an arbitrary DC offset, A is the amplitude of the ring-down waveform. The ring-down decay constant, $\tau$, is inversely proportional to absorbance within the optical cavity. An absorption spectrum for the sample can be obtained by plotting the ring-down rate R, or the reciprocal of the ring-down decay constant $1/\tau$, versus the wavelength $\lambda$ of the incident light. In practice, the decay constant $\tau$ is almost universally determined by: digitizing the signal at the cavity output; and fitting individual or average ring-down waveforms to a three-parameter function using a non-linear least squares fitting routine.

Further details of a system for analysing an absorbance signal are set out in International (PCT) Patent Application Publication No. WO 2012/021943 (PCT/AU2011/001071) published on 23 February in the name of NewSouth Innovations Pty Limited et al, which is incorporated herein by reference.

Real-Time Determination of Ringdown Decay Time

Figures 7A, 7B, 7C:
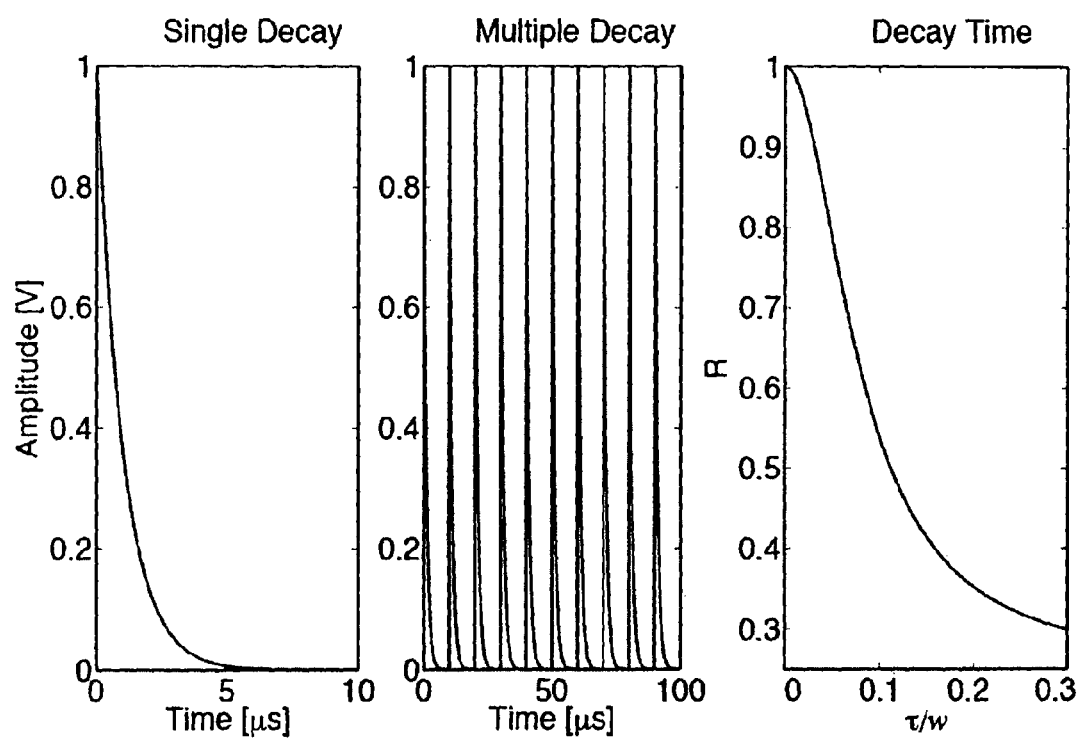
FIGS. 7A, 7B, and 7C are plots of a single exponential decay, multiple (10) consecutive exponential decays, and the decay time relationship between τ and R as a function of the data collection window w, respectively.

A process of harmonic data extraction for ring-down decay time constant $\tau$ is described hereinafter. In this description, ten consecutive exponential decays were collected and analysed, as shown in FIG. 7. An expression for $\tau$ relative to the magnitudes of the fundamental and first harmonic frequency components of the pulse is obtained. The following mathematical model is used for the signal:

$$S(t) = \sum_{k=1}^{10} S_k(t), \quad 0 \le t \le 10w,$$

where $$S_k(t) = \begin{cases} I_0 e^{-(t-(k-1)w)/\tau} + O & \text{if } (k-1)w \le t \le kw \\ 0 & \text{otherwise} \end{cases}.$$

Here, w is the sampling window for a single decay, and in the case of a pulsed laser excitation refers to the time between two consecutive pulses. Multiplying S(t) with $$\cos\left(2\pi \frac{t}{w}\right) \text{ and } \cos\left(4\pi \frac{t}{w}\right)$$

and integrating between 0 and 10 w results in $$A_1 = \int_0^{10w} S(t)\cos\left(2\pi \frac{t}{w}\right) dt$$
$$= 10 \int_0^w (I_0 e^{-t/\tau} + O)\cos\left(2\pi \frac{t}{w}\right) dt$$
$$= -10 I_0 \tau w^2 \frac{e^{-\frac{w}{\tau}} - 1}{w^2 + 4\pi^2 \tau^2}$$

and $$A_2 = \int_0^{10w} S(t)\cos\left(4\pi \frac{t}{w}\right) dt$$
$$= 10 \int_0^w (I_0 e^{-t/\tau} + O)\cos\left(4\pi \frac{t}{w}\right) dt$$
$$= -10 I_0 \tau w^2 \frac{e^{-\frac{w}{\tau}} - 1}{w^2 + 16\pi^2 \tau^2}.$$

Furthermore, $$R = \frac{A_2}{A_1} = \frac{w^2 + 4\pi^2 \tau^2}{w^2 + 16\pi^2 \tau^2}. \quad (2)$$

Equation (2) can be solved for $\tau$, giving:

$$\tau = \frac{w}{2\pi} \sqrt{\frac{1-R}{4R-1}}. \quad (3)$$

This technique is independent of the initial light intensity $I_0$ and the DC offset O and can be applied to the analysis of any number of exponential decays (not just 10 ringdowns) as Equations (2) and (3) relate w, R, and $\tau$ only. Furthermore, w can be adjusted to ensure that empty cavity value for $\tau$ is greater than 4R and hence in the stable region.

The absorbance, A, can then be determined from the relation:

$$A = -\log(T) = \log\left(\frac{I_0}{I}\right) = \frac{n \times l}{2.303 \times c} \left(\frac{1}{\tau} - \frac{1}{\tau_0}\right) \quad (4)$$

where T is the transmittance, I is the transmitted intensity, n is the index of refraction within the optical cavity, l is the optical path length in the cavity, c is the speed of light, and $\tau_0$ is the empty cavity decay lifetime.

This section described the process required to determine $\tau$ from one laser source. In the following section, these concepts are extended to produce a system with multiple lasers connected to the same reflectivity cavities and/or multiple reflectivity cavities with the same laser source.

Real-Time Laser-Based Spectrometer System

FIG. 1 illustrates a real-time laser-based spectrometer system 100, which is in this case excited by a single pulsed laser system, with which embodiments of the invention may be practiced, capable of measuring quantum transitions. The system 100 shown in FIG. 1 is a derivative of cavity ringdown spectroscopy (CRDS) and illustrates the digital manifestation of an embodiment of the invention, but the scope of the invention is not so limited. The system 100 can be constructed with analog components readily. An analog system may be practiced using lockin amplifiers/mixer to perform the mixing process. In CRDS, light generated by a laser source is trapped in a detection cavity with high reflectivity. The intensity of the detected signal decays exponentially according to Equation (1). $\tau$ is the cavity ringdown time and can be used to generate a spectrum for a given sample by scanning the laser wavelength and recording $\tau$ at each wavelength.

The system 100 includes a laser 110, a vacuum and optical cell or optical ringdown cavity 120, one or more photodetectors 130, a control module 140 (that controls the laser source 110 and/or vacuum and optical cell 120), and an absorbance analysis module 160. The laser control module 140 controls how the laser scans, vacuum is removed from the cell 120, and times various operations, such as the initial setup of the laser 110. The absorbance analysis module 160, receives and reads digital data 150, graphs data, measures the power of harmonics, estimates $\tau$, generates power spectrum, and determines species by comparing spectra with a library of spectra for known elements. The vacuum and optical cell 120 has four input/output couplers 121A, 121B, 121C, and 121D. As shown in FIG. 1, the light beam 112 from the laser source 110 is input to the input coupler 121A of the cell 120. The output of the cell 120 is provided by output coupler 121D. The couplers 121B and 121C are unused in FIG. 1, but this need not be the case. The vacuum and optical cell 120 is a symmetric system.

Figure 5:
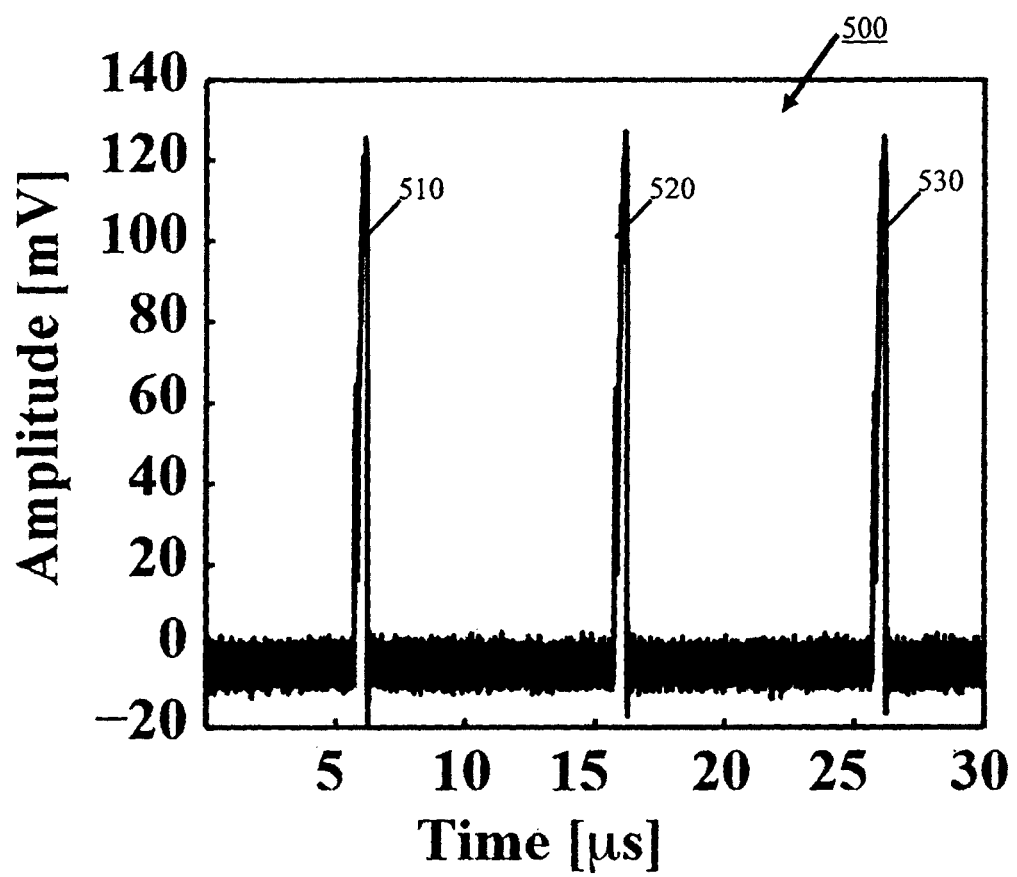
FIG. 5 is plot of the quantum cascade laser pulses when operating at 100 kHz, as measured on an mercury-cadmium-telluride (MCT) detector; the pulse train signal coming from a commercially available tunable mid-IR external cavity laser system.

The tunable laser 110 can be frequency tuned over a vast wavelength range. The laser 110 may be one or more pulsed, quantum cascade lasers (QCL), or other pulsed laser medium, or continuous wave laser system that is modulated appropriately. The pulse train for a typical laser running with a 100 kHz repetition rate and 0.5 µs pulse width is shown in FIG. 5. A plot 500 of three pulses 510, 520, and 530, each with an amplitude of slightly more than 120 mV, occurs 10 µs apart at approximately 6, 16 and 26 µs are shown. The vacuum and optical cell (cavity) 120 is vacuum compatible with suitable photodetectors 130. While optical coating technology does exist to make high finesse cavities in this wavelength range, no single sets of mirrors are available to cover the entire range of wavelength. As shown in FIG. 1, a light beam 112 generated by the laser 110 is input to the vacuum and optical cell 120 at the input coupler 121A. In the system 100, mode matching optics (MMO) 114A, 114B and a mirror 116 are used to steer the light beam 112 into the vacuum and optical cell 120.

Figure 6:
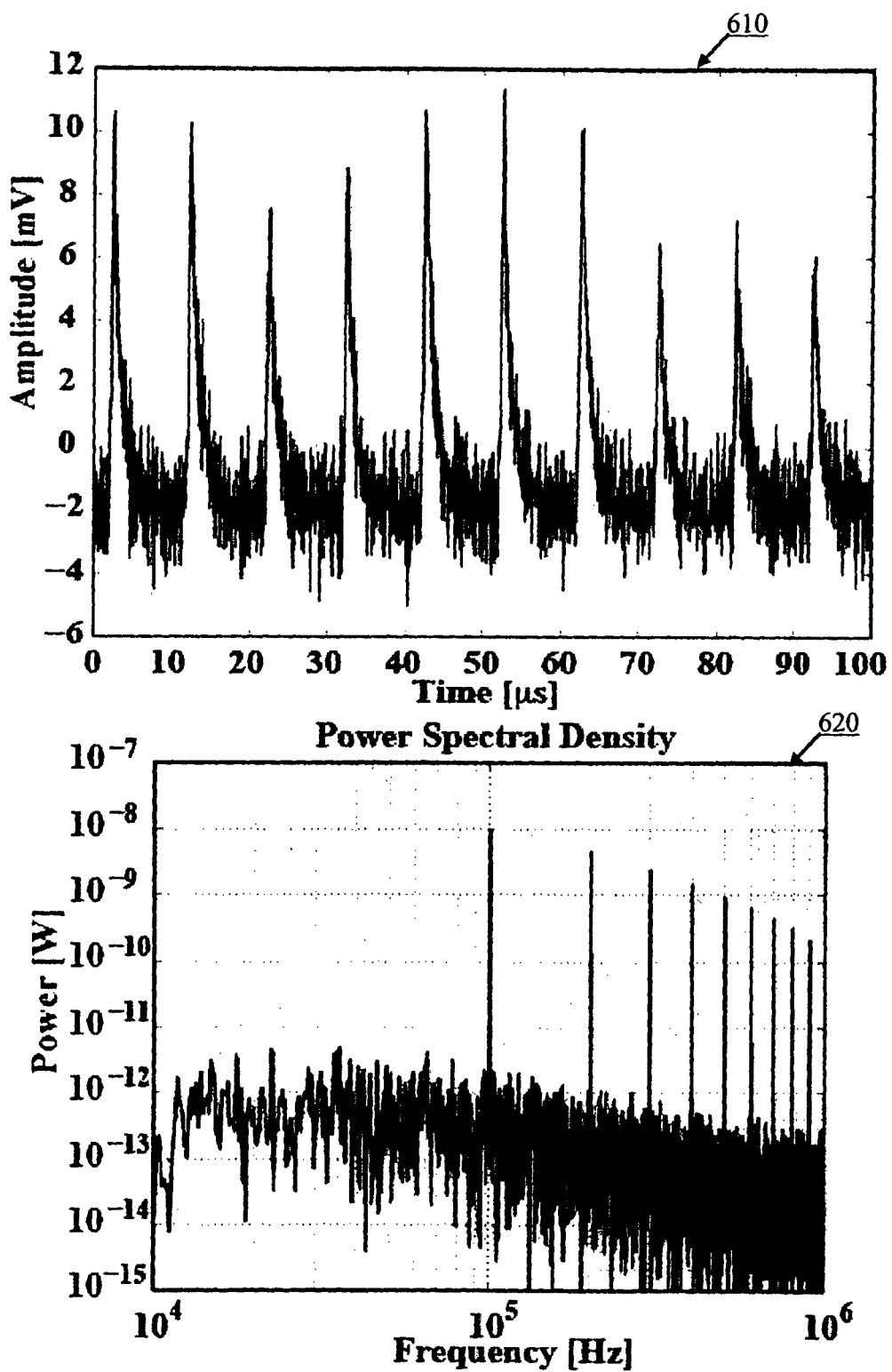
FIG. 6 comprises two plots showing the time and frequency characteristics measured after the optical cavity by an MCT detector, the QCL cavity ringdown signals operating at 100 kHz repetition rate and at a wavelength of 5940 nm, as measured from a ring optical cavity with optical path length of 2 m with two input/output couplers of 99.8% and two HR, =99.995% turning mirrors.

FIG. 1 indicates that the light beam 112 is reflected several times in the optical ringdown cavity 120 before being output via coupler 121D as the CRDS signal 122 to the photodetector 130. The output of the cavity 120 is the CRDS signal 122. The photodetector 130 produces the detected CRDS signal or photocurrent 132, an analog electrical signal output, shown in FIG. 6 (top: time trace 610; bottom: power spectrum 620), to a control module 140, and in particular a data acquisition system (DAQ) 142 of the control module 140. The time trace 610 illustrates 10 pulses at 10 µs intervals, and the power spectral density 620 shows the power of spectra as a function of frequency. The DAQ 142 performs analog-to-digital conversion of the photocurrent 132. The digital signal or digital bitstream 150 comprising digital data based on the detected photocurrent 132 produced by the DAQ 142 is output to a control system 144 of the control module, and in turn to control electronics 146. The control system 144 and electronics 146 produce signals that can be used to adjust the parameters of the system 100. The control electronics 146 controls the digital-to-analog converters and amplifiers 148, which provide one or more control signals and other signals 152 from the control module 140 to the laser 110 to generate the light beam 112. Control signals may also be provided to the vacuum and optical cell 120 (not shown in FIG. 1). The signals 152 generated by the digital-to-analog converters and amplifiers 148 drive the system components, such as the piezo electric transducers (PZTs) of the laser 110.

The digital signal or digital bitstream 150 comprising digital data based on the detected photocurrent 132 produced by the DAQ 142 is input to the absorbance analysis module 160, and in particular to a data processing module 162. The data processing module 164 interfaces with a module for estimating $\tau$. The data processing techniques implemented in module 162 extract information from the DAQ 142 to produce the estimate for the cavity ringdown time $\tau$. Using the estimate of $\tau$, a module 166 for generating rapidly a spectrum 166 is coupled to the module 164, and in turn a module for determining species concentration 168 is coupled to module 166. The module 166 produces the absorbance signal (e.g., where the y-axis is absorbance and the x-axis is laser wavelength). The module 168 detects an absorbing species in the sample.

The system 100 shown in FIG. 1 comprises a control loop 140 and an estimation loop 160. The control loop 140 controls the laser 110 and cavity scan dynamics, so that efficient intensity build-up in the cavity 120 and ringdowns can be achieved. Under pulsed laser operation, the control system 144 simply scans the laser 110 through its tuning range. If CW laser operation were used instead, the control loop 140 would also need to make corrections to the laser 110 and cavity 120 to be in continuous lock throughout the scanning process. The estimation loop 160 determines the ring-down time, $\tau$, (or an equivalent quantity) as a function of wavelength, and hence the absorption spectrum.

Figure 4:
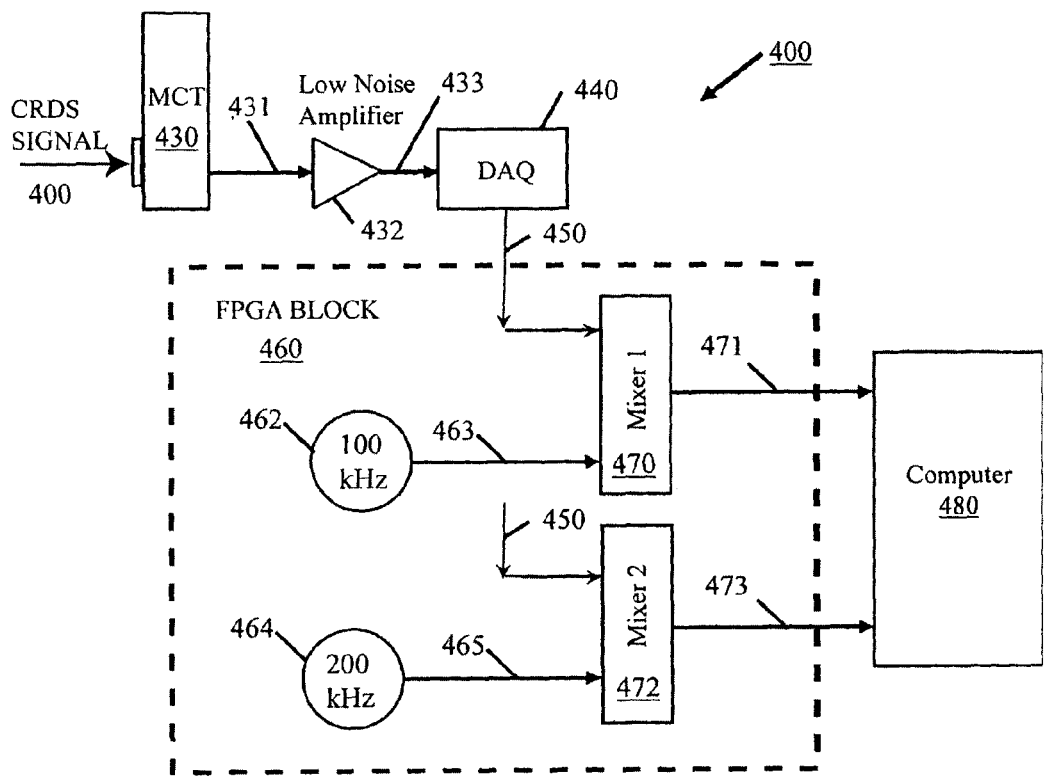
FIG. 4 is a block diagram illustrating a general data-processing system to determine from a 100 kHz pulse rate laser source, which can be practiced with the system of FIG. 1.

FIG. 4 is a block diagram illustrating a general data-processing system 400 required to determine $\tau$ from a 100 kHz (f) pulse rate laser source (not shown in FIG. 4), which can be practiced with the system of FIG. 1. FIG. 4 shows schematically a particular implementation of the data processing system 400, in which a detector signal or photocurrent 431 is produced by a photodetector and in particular a mercury-cadmium-telluride (MCT) detector 430 from a CRDS signal 422 output by the vacuum and optical cell (not shown in FIG. 4; see cell 120, producing signal 122). The detector signal 431 output by the MCT 430 is amplified appropriately. In FIG. 4, a low noise amplifier (LNA) 432 does this. The output of the LNA 432 is an amplified photocurrent 433 sent to the DAQ 440, which digitizes the signals to provide an acquired (digital) signal (or digital bitstream) 450 (this corresponds to signal 150 of FIG. 1). The digital signal 450 can be input to a field programmable gate array (FPGA) 460, in this implementation. The FPGA block 460 comprises signal sources 462 and 464 and mixers 470 and 472. The fundamental, f, and second harmonic, 2f, powers are calculated by first and second mixers 470 and 472 (in practice these are multiplication stages). The digital signal 450 is mixed with 100 kHz and 200 kHz generated signals (f and 2f) by mixers 470 and 472, respectively. The outputs 471, 473 of the mixers 470 and 472 are provided from the FPGA block 460 to a computer 480. The computer 480 determines the ratio of the time domain magnitude, f/2f and hence τ, as determined by Equation (3). The suitably programmed computer 480 calculates the ratio and produces an absorption spectrum. While the first and second harmonics have been discussed here, the embodiments of the invention may be practiced using different harmonics and combinations of harmonics. For example, the first and third harmonic might be used. Alternatively, a combination of harmonics might be used such as (second harmonic plus third harmonic) divided by first harmonic.

Multiplexed Spectroscopy Absorbance

The embodiments of the invention provide methods and optical detection systems for generating and processing a real-time time-domain cavity ringdown spectroscopy (CRDS) signal from an absorbing species in an optical detection system having an optical ringdown cavity. The optical ringdown cavity is adapted for accepting a sample of an absorbing species. The embodiments of the invention multiplex beamlines in the optical ringdown cavity.

In one embodiment, modulated light signals are generated using a number of light sources having different wavelengths. The light sources are pulsed at specified pulse rates. The modulated light signals are resonated using the optical ringdown cavity comprising mirrors to produce the CRDS signal. Each mirror has the same or substantially the same reflectivity. The selectivity of the mirrors is dependent upon the pulse rate of the modulated light signals. Different beamlines are established by the modulated light signals and the mirrors interacting with the absorbing species sample. The method may further comprise: detecting the CRDS signal output by the optical ringdown cavity for the multiplexed modulated light signals; and estimating the cavity ringdown times τ and determining spectra for the absorbing species sample from the detected CRDS signal by mixing the detected CRDS signal dependent upon the wavelengths and the selected harmonics of the modulated light signals from the light sources.

In another embodiment, a modulated light signal is generated using a light source. The light source is pulsed at a specified pulse rate. The modulated light signal is resonated using the optical ringdown cavity comprising a number of sets of mirrors to produce the CRDS signal. Each set of mirrors has the same or substantially the same reflectivity. The selectivity of the mirrors is dependent upon the pulse rate of the modulated light signal. Different beamlines are established by the modulated light signal and the mirrors interacting with the absorbing species sample. The method may further comprise: detecting the CRDS signal output by the optical ringdown cavity for the multiplexed beamlines; and estimating the cavity ringdown times τ and determining spectra for the absorbing species sample from the detected CRDS signal by mixing the detected CRDS signal dependent the selected harmonics of the modulated light signal from the light source.

In a further embodiment, modulated light signals are generated using a number of light sources having different wavelengths. The light sources are pulsed at specified pulse rates. The modulated light signals are resonated using the optical ringdown cavity comprising a number of sets of mirrors to produce the CRDS signal. Each set of mirrors has the same or substantially the same reflectivity. The selectivity of the mirrors is dependent upon the pulse rates of the modulated light signals. Different beamlines are established by the modulated light signals and the mirrors interacting with the absorbing species sample. The method may further comprise: detecting the CRDS signal output by the optical ringdown cavity for the multiplexed beamlines; and estimating the cavity ringdown times and determining spectra for the absorbing species sample from the detected CRDS signal by mixing the detected absorbance signal CRDS dependent upon the wavelengths and the selected harmonics of the modulated light signals from the light sources.

Different beamlines may be adjusted such that the reflectivities of input and output mirrors of the optical ringdown cavity are different for each beamline.

The estimating step may comprise calculating the power of selected harmonics using mixers and signal sources for the selected harmonics. The spectra determining step may comprise plotting the ring-down rate R or the reciprocal of the ring-down decay constant 1/τ versus the wavelength λ of the incident light. The absorbing species may be identified by comparing the determined spectra for the absorbing species sample with a library of predetermined spectra for known elements. The multiplexed beamlines using mirrors with selected reflectivities and the use of matching pulse rate of the light sources allows the estimating and determining steps to be optimally processed.

The method may further comprise controlling dependent upon the detected CRDS signal the one or more light sources and/or the optical ringdown cavity.

Extension of the Measurement Wavelength Range

The embodiments of the invention improve measurement absorbance dynamic range and measurement wavelength range. Doing so improves the system 100 and makes the system 100 more versatile. Also the cost of the system 100 may be lowered through the use of less expensive lasers 100.

Figure 8:
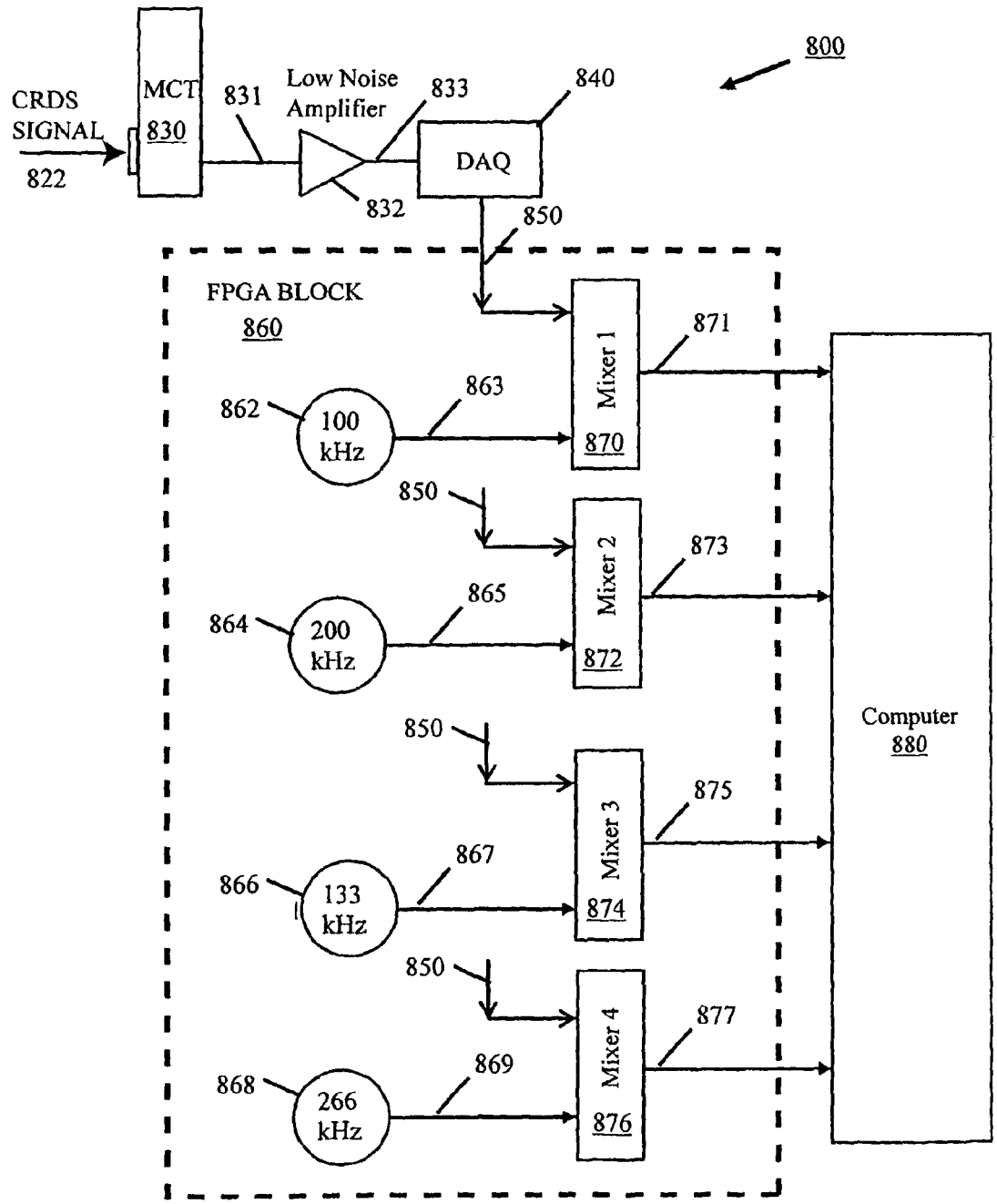
FIG. 8 is a block diagram illustrating a general data-processing system to determine τ from 100 kHz, 200 kHz, 133 kHz, and 266 kHz pulse-rate laser sources (third data path not shown), which may be practiced with the system of FIG. 2 having three beamlines.

The system 100 of FIG. 1 is implemented using an optical cavity 120 with 4 mirrors, separated by 50 cm and in a FIG. 8 configuration. Two of the mirrors have finesse 99.8% reflectivity and the other 2 have 99.995% reflectivity, giving a cavity ring-down time of ≈3 µs. The quantum cascade laser 110 may be run in pulsed mode with a 100 ns pulse width and 10 µs repetition time. Hence, the CRDS signals are repeated at a 100 kHz rate (the maximum rate for this laser). Under these conditions, the absorbance measurement range is determined to be from ≈$5\times10^{-6}$ to ≈$5\times10^{-4}$.

Figure 2A:
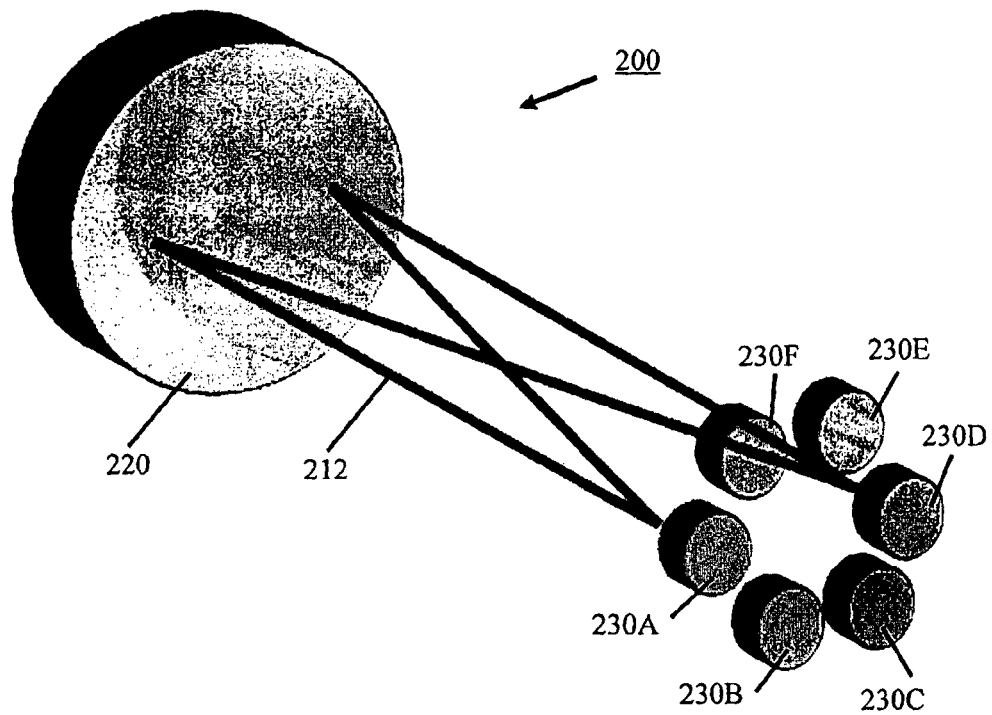
FIGS. 2A and 2B are block diagrams illustrating the combination of multiple laser sources of different wavelength tuning ranges (with the same mirror reflectivity for each wavelength range) in the same vacuum and optical cell to form a wider wavelength range spectrometer.
Figure 2B:
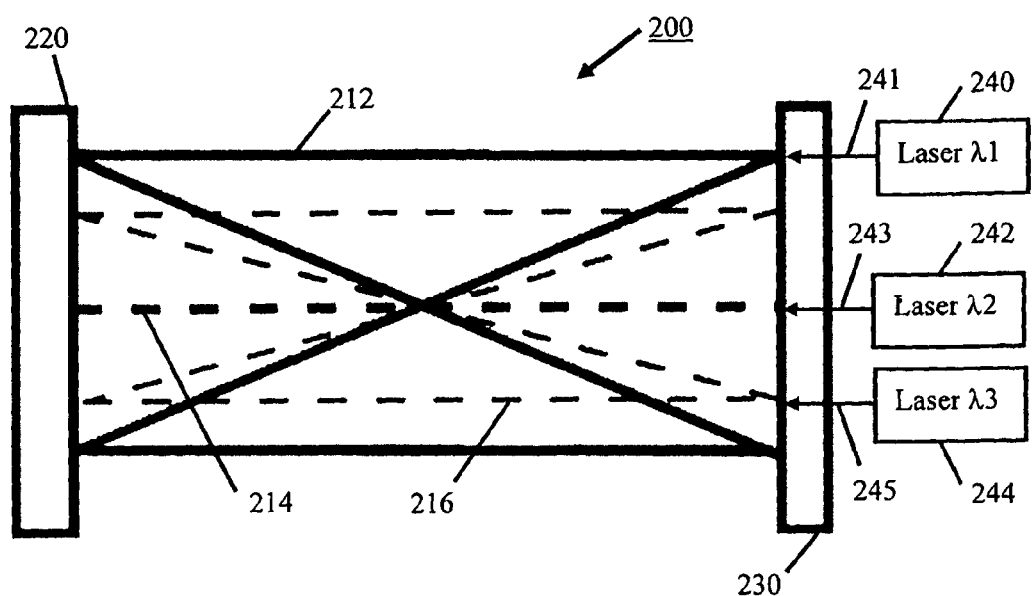

To widen the absorbance dynamic range, the system 100 of FIG. 1 is modified using the configuration 200 shown in FIG. 2 to implement an improved system. In the configuration 200 of FIG. 2, multiple beams or beamlines 212, 214, 216 (thick solid, thick dashed, and thin dashed lines, respectively, in FIG. 2B) pass through the sample, each in figure-8 paths. Relevant wavelengths include visible light to infrared (IR). Different beamlines may have different wavelengths. Any combination of wavelength from visible light to IR may be practised. The wavelength ranges do not have to be continuous. In FIG. 2B, multiple light beams 241, 243, 245 are generated by three lasers 240, 242, and 244 at wavelengths λ1, λ2, and λ3, respectively. The multiple modulated light signals 241, 243, 245 establish beamlines 212, 214, 216 in the cavity resonating between mirrors. A single beam 212 is shown in FIG. 2A to simplify the drawing only; the other beams 214 and 216 are shown in FIG. 2B. The mirrors 230A-230F have the same reflectivity, e.g. 99.8%. The different beamlines 212, 214, 216, although interacting with the same sample, can be adjusted such that the reflectivity of the input and output mirrors are different for each beamline. The configuration 200 of FIG. 2 is one implementation in which small reflectors 230A-230F are used at one end with one large reflector 220 at the other end, or the system can be configured symmetrically with reflector 220 being small identical reflectors to 230A-230F. Alternatively, the mirror configuration can be constructed with more or less reflection, or with varying size or thickness mirrors. Thus, the reflectivities of the mirrors 220 and 230A-230F may have the same or slightly different reflectivities. The mirrors do not have exactly the same reflectivity since the coating process is not completely accurate. However, the reflectivities do not need to be matched as best they can in the coating process such that the ring-down time for each set of mirrors is approximately constant over the wavelength range of the laser scan. In the configuration 200 of FIG. 2A, a first beamline is established with mirrors 230A, 220, 230D, 220, and 230A; a second beamline is established with mirrors 230B, 220, 230E, 220, and 230B (not shown in FIG. 2A); and a third beamline is established with mirrors 230C, 220, 230F, 220, and 230C (not shown in FIG. 2A).

The measurement wavelength range can be extended from the configuration shown in FIG. 1 by using different lasers 240, 242, 244 for each beamline 212, 214, 216 in FIG. 2. In this case, using 3 beamlines, the mirror reflectivities of each beamline 212, 214, 216 can be adjusted to cover the wavelength range of each laser source 240, 242, 244 with the emphasis of maintaining the same ring-down time (approximately) for each beamline 212, 214, 216. Each laser source 240, 242, 244 can be pulsed at a unique rate such that the demodulation process can uniquely identify each laser source 240, 242, 244. The data processing for this implementation differs from that shown in FIG. 4, as shown in FIG. 8.

FIG. 8 is a block diagram illustrating a general data-processing system 800 comprising two sets of demodulation paths in a single FPGA unit 860 (corresponding to 2 beam lines). However, the system 800 can be adjusted to as many beamlines as required. Once again, all signals can be measured simultaneously using this multiplexed approach. The data-processing system 800 of FIG. 8 may be practiced with the system of FIG. 2. The data processing system 800 is described hereinafter with reference to two data paths, but only for the ease of depiction is this the case. A third data path (not shown) for the third beamline, operating at possibly 166 kHz, can be similarly implemented and configured to be used with the system 200 of FIG. 2.

The data-processing system 800 can be used to determine τ from 100 kHz (f1) and 133 kHz (f2) pulse rate laser sources. Again, a CRDS signal 822 from the cavity (not shown) is input to a photodetector 830 (MCT detector). A detector signal 831 is produced by MCT 830 from the CRDS signal 822 output by the vacuum and optical cell (not shown in FIG. 8; see cell 120, producing signal 122). The CRDS signal 822 is dependent upon the 100 kHz (f1) and 133 kHz (f2) pulsed beams. The detector signal 831 output by the MCT 830 is amplified appropriately. This is done by a low noise amplifier (LNA) 832 in FIG. 8. The output 833 of the LNA 832 is sent to the DAQ 840 that digitizes the signals to provide digital signal 850. The digital signal 850 can be input to a field programmable gate array (FPGA) 860, in this implementation. The FPGA block 860 comprises several signal sources 862, 864, 866, and 868 and mixers 870, 872, 874, and 876. The fundamental, f1, and second harmonic, 2f1, powers are calculated by first and second mixers 870 and 872. The digital signal 850 is mixed with 100 kHz and 200 kHz generated signals (f1 and 2f1) by mixers 870 and 872, respectively. The outputs 871 and 873 of the mixers 870 and 872 are provided from the FPGA block 860 to a computer 880. Likewise, the fundamental, f2, and second harmonic, 2f2, powers are calculated by third and fourth mixers 874 and 876. The digital signal 850 is mixed with 133 kHz and 266 kHz generated signals (f2 and 2f2) by mixers 874 and 876, respectively. The outputs 875 and 877 of the mixers 874 and 876 are provided from the FPGA block 860 to the computer 880. In this manner, the FPGA 860 can be used to process multiplexed laser beams passing through the sample. The computer 880 performs the same type of processing as computer 480 in FIG. 4, with suitable adjustments for multiple wavelength beams. The computer 880 determines the ratio of the magnitude, f1/2f1 and the ratio of the magnitude, f2/2f2 and hence τ, as determined by Equation (3). The suitably programmed computer 880 calculates the ratio and produces an absorption spectrum.

Extension of the Absorbance Dynamic Range

The resulting ring down time for each beamline can be adjusted to meet a specific absorbance range, and the laser pulse rate can be increased or decreased to optimise the detection window for each beamline and ring down time. Additionally, the output signal can be collected on a single detector and with each beamline being detected simultaneously, as long as the laser pulse rate for each beamline is intentionally set to be different, by simultaneous demodulation of each fundamental and harmonic for each beamline respectively.

Figure 3A:
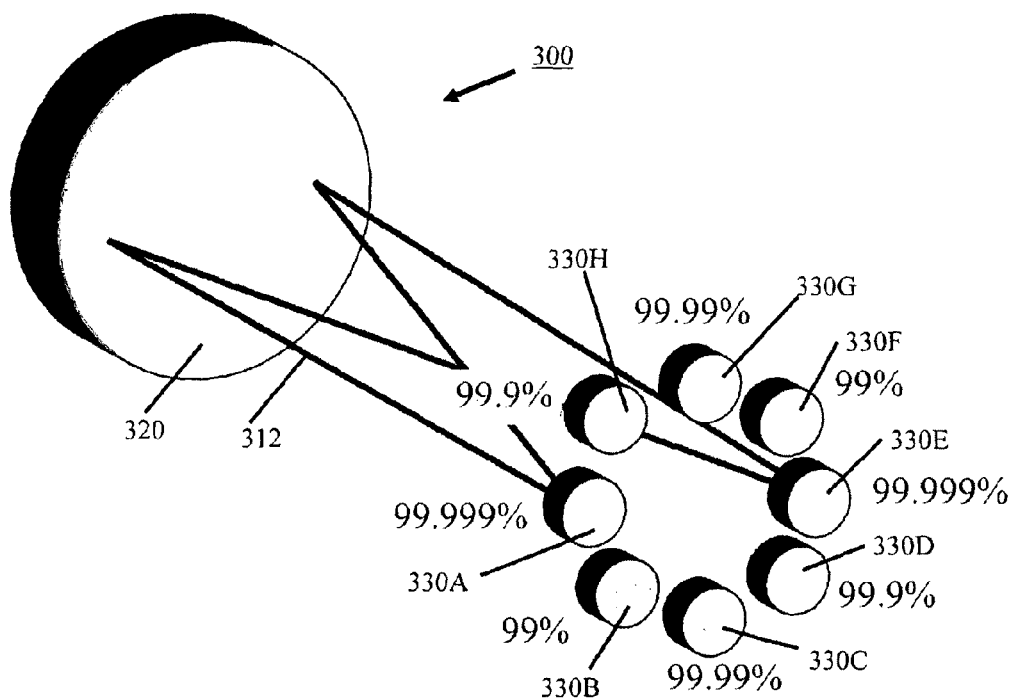
FIGS. 3A and 3B are block diagrams illustrating the combination of different mirror reflectivity sets for use with a single laser source to create a wide dynamic range spectrometer.
Figure 3B:
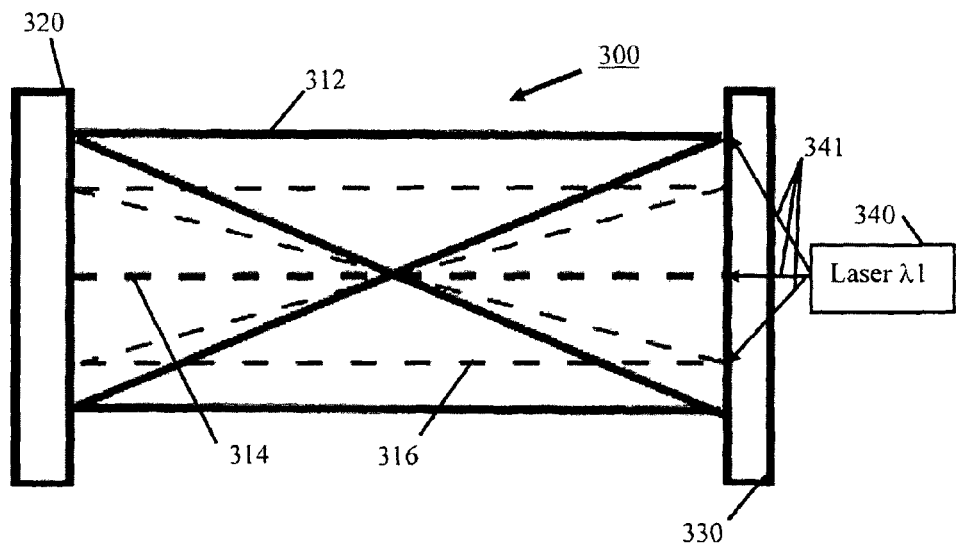

The measurement dynamic range can be extended from the configuration shown in FIG. 1 by using the configuration 300 having different mirror reflectivity sets for each beamline, as shown in FIG. 3. In this case 300, using 3 beamlines, the mirror reflectivities of each beamline can be adjusted, to cover a different ring-down time for the same laser source. Multiple beams 312, 314, 316 (thick solid, thick dashed, and thin dashed lines, respectively, in FIG. 3B) pass through the sample, each in figure-8 paths. In FIG. 3B, multiple light beams 312, 314, and 316 are generated by a modulated light signal 341 output from a single laser 340 at wavelength λ1. A fourth-light beam is not depicted in FIG. 3B to simplify the drawing, and the system could comprise as many beamlines as required as long as they can fit in the space available. A single beam 312 is shown in FIG. 3A to simplify the drawing only. The sets of mirrors 330A-330H have different reflectivities as follows:

| Mirror No. | Reflectivity |
|---|---|
| 330A | 99.999% |
| 330B | 99% |
| 330C | 99.99% |
| 330D | 99.9% |
| 330E | 99.999% |
| 330F | 99% |
| 330G | 99.99% |
| 330H | 99.9% |

The configuration 300 of FIG. 3 is one implementation in which small reflectors 330A-330H are used at one end with one large reflector 320 at the other end, or the system can be configured symmetrically with reflector 320 being small identical reflectors to 330A-330H. In the configuration 300 of FIG. 3A, a first beamline is established by sets of mirrors 330A, 320, 330E, 320, and 330A with some mirrors having the same reflectivity; a second beamline is established by sets of mirrors 330B, 220, 330F, 320, and 330B (not shown in FIG. 3A) with some mirrors having the same reflectivity; a third beamline is established by sets of mirrors 330C, 320, 330G, 320, and 330C (not shown in FIG. 2A) with some mirrors having the same reflectivity; and a fourth beamline is established by sets of mirrors 330D, 320, 330H, 320, and 330D (not shown in FIG. 2A) with some mirrors having the same reflectivity. The same laser 340 is used for all beam paths in FIG. 3, but the laser pulse rate is adjusted in the data processing for each set of mirrors. Please note that in this case the beamlines are physically separated and each beamline is symmetrically distributed around the cavity axis. In general however, the beamlines can be constructed in any configuration that is appropriate to generate the appropriate ring-down times.

As opposed to the configuration 200 of FIG. 2, FIG. 3 shows that the ring-down time for each beamline is intentionally altered so that the absorbance range is shifted. The laser source, therefore, must be pulsed at a unique rate for each beamline such that the relation derived in Equation (3) is maximized. The embodiment shown in FIG. 3 is advantageous in that the system has wider sensitivity. The pulse repetition rate can be matched to the reflectivity of sets of mirrors. Lower reflectivity requires faster pulses, while greater reflectivity requires slower pulses.

Figure 9:
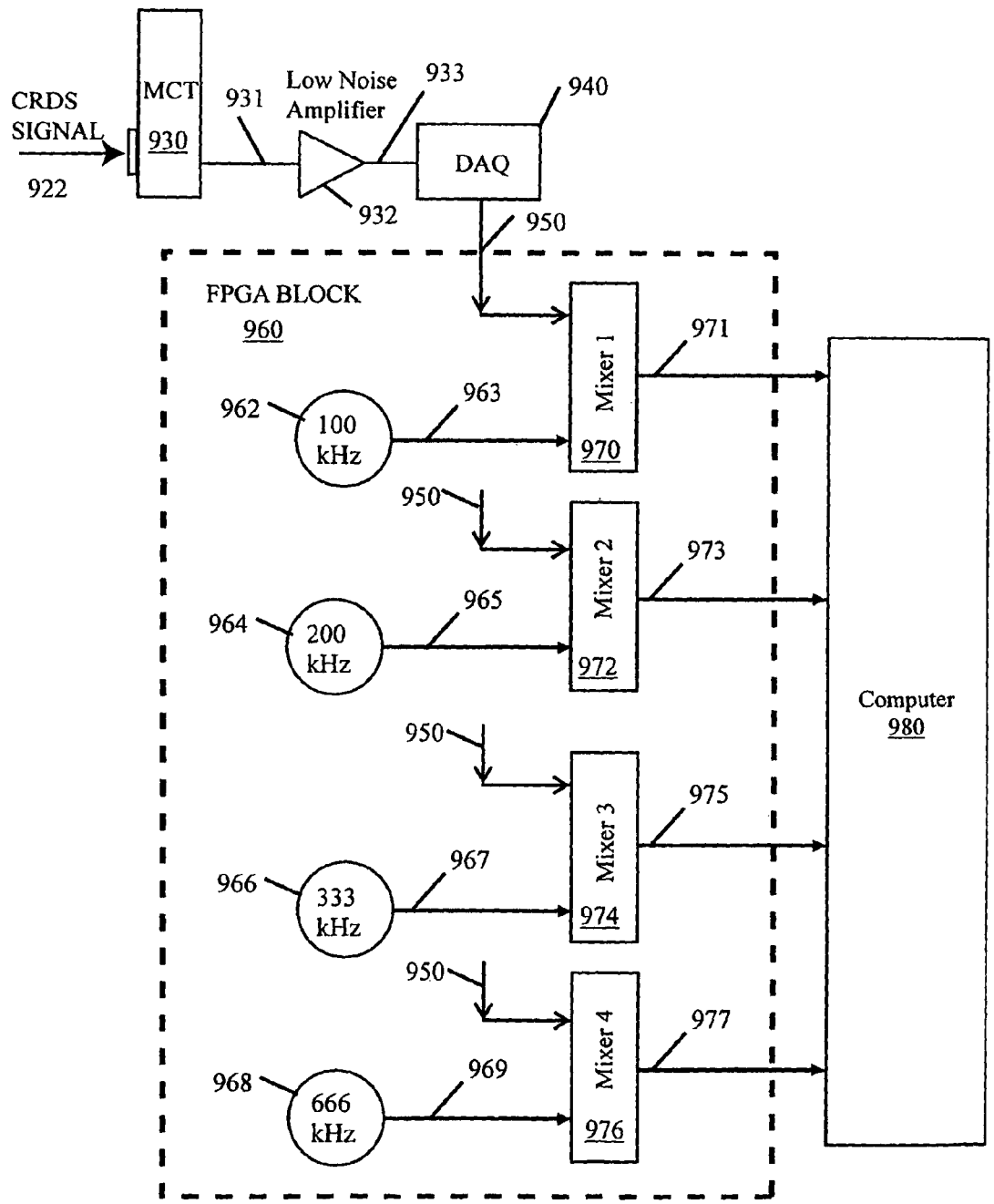
FIG. 9 is a block diagram illustrating a general data-processing system to determine τ from 100 kHz, 200 kHz, 333 kHz, and 666 kHz pulse-rate laser sources (other data paths are not shown to simplify the drawing), which may be practiced with the system of FIG. 3 having four beamlines generated from a single laser.

The data processing for this implementation differs from that shown in FIGS. 4 and 8 as shown in FIG. 9 only in that the pulse rate of the laser source is changed for each beamline configuration. That is, the laser source needs to be operated sequentially at a unique pulse rate for each beamline such that Equations (2) and (3) are maximized.

FIG. 9 is a block diagram illustrating a general data-processing system 900 showing two sets of demodulation paths in the single FPGA unit 940 (corresponding to 2 beam lines) but this can be adjusted to as many lines as required. The data processing system 900 may be practiced with the system 300 of FIG. 3, in which case four data paths would be implemented in the system 900. These further data pathways are not shown in FIG. 9 only to simplify the drawing.

Once again, all signals can be measured simultaneously using this multiplexed approach. The data-processing system 900 can be used to determine $\tau$ from 100 kHz (f1) and 333 kHz (f3) pulse rate laser sources. Again, a detector signal 931 is produced by MCT 930 from CRDS signal 922 output by the vacuum and optical cell (not shown in FIG. 9; see cell 120, producing signal 122). The CRDS signal 922 is dependent upon the 100 kHz (f1) and 333 kHz (f3) pulsed beams. The detector signal 931 output by the MCT 930 is amplified appropriately. This is done by a low noise amplifier (LNA) 932 in FIG. 9. The output 933 of the LNA 932 is sent to the DAQ 940 that digitizes the signals 933 to provide digital signal 950. The digital signal 950 can be input to a field programmable gate array (FPGA) 960, in this implementation. The FPGA block 960 comprises several signal sources 962, 964, 966, and 968 and mixers 970, 972, 974, and 976. The fundamental, f1, and second harmonic, 2f1, powers are calculated by first and second mixers 970 and 972. The digital signal 950 is mixed with 100 kHz and 200 kHz generated signals (f1 and 2f1) by mixers 970 and 972, respectively. The outputs 971 and 973 of the mixers 970 and 972 are provided from the FPGA block 960 to a computer 980. Likewise, the fundamental, f3, and second harmonic, 2f3, where f3>>f1, powers are calculated by third and fourth mixers 974 and 976. The digital signal 950 is mixed with 333 kHz and 666 kHz generated signals (f3 and 2f3) by mixers 974 and 976, respectively. The outputs 975 and 977 of the mixers 974 and 976 are provided from the FPGA block 960 to the computer 980. In this manner, the FPGA 960 can be used to process multiplexed laser beams passing through the sample. The computer 980 performs the same type of processing as computer 480 in FIG. 4, with suitable adjustments for multiple wavelength beams. The computer 980 determines the ratio of the magnitude, f1/2f1 and the ratio of the magnitude, f3/2f3 and hence $\tau$, as determined by Equation (3). The suitably programmed computer 980 calculates the ratio and produces an absorption spectrum.

In this case each beamline is demodulated at large frequency differences because the fundamental frequency occurs at each pulse unique pulse rate of the laser source. Once again, all signals can be measured simultaneously using this multiplexed approach.

Figure 10:
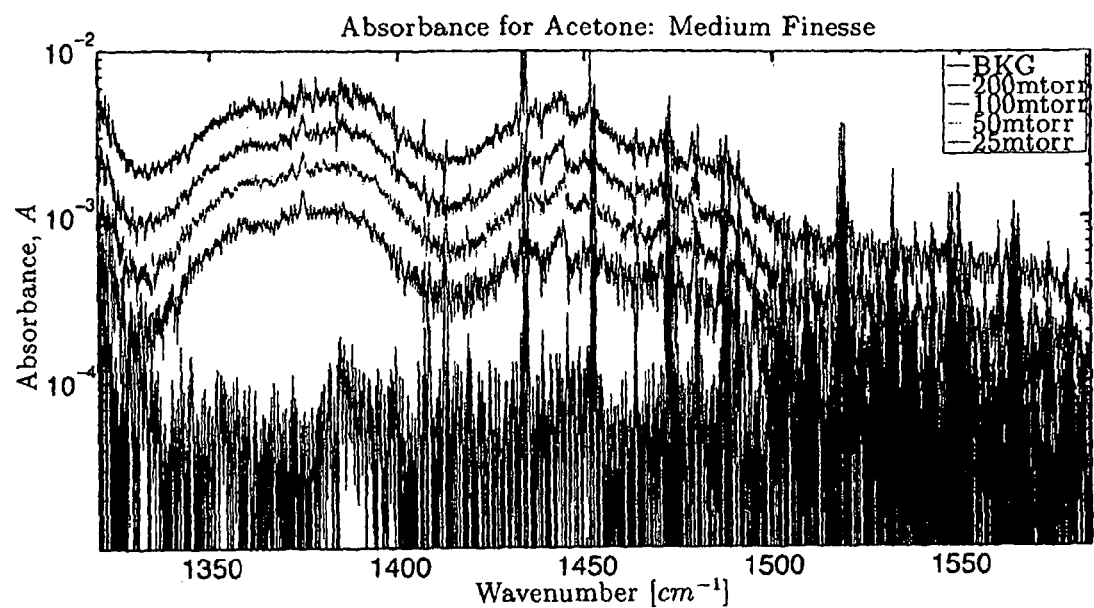
FIG. 10 is a plot showing the absorbance A as a function of wavenumber for acetone using a medium finesse cavity, showing the dynamic range increasing when using the same QCL laser working in pulse mode with different reflectivity mirrors.
Figure 11:
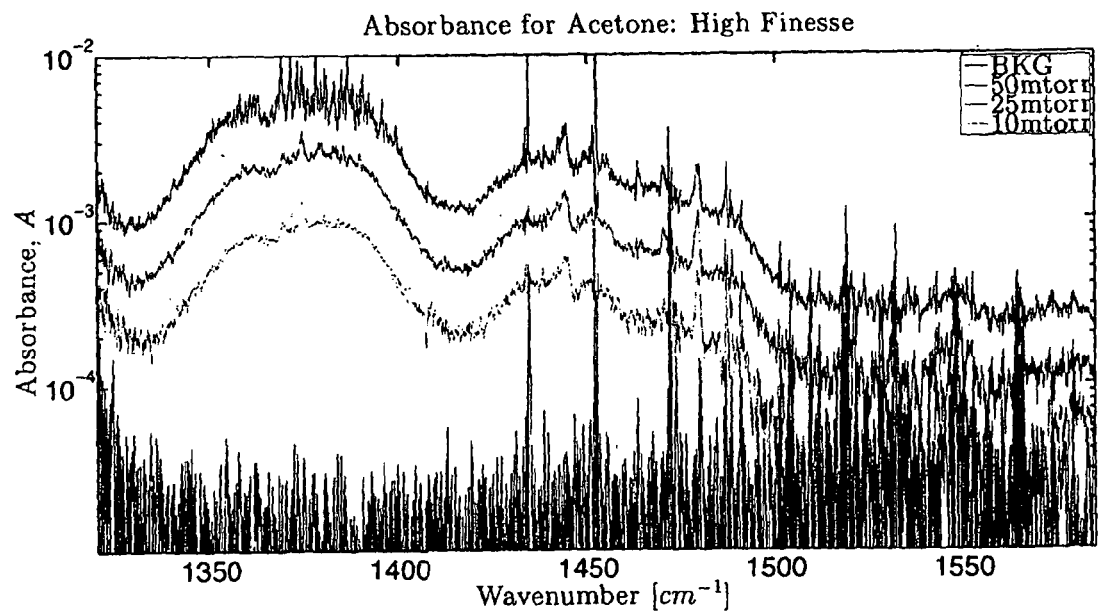
FIG. 11 is a plot showing the absorbance A as a function of wavenumber for acetone using a high finesse cavity, showing the dynamic range increasing when using the same QCL laser working in pulse mode with different reflectivity mirrors.

FIGS. 10 and 11 illustrate the sensitivity of the techniques described hereinbefore. FIG. 10 illustrates medium sensitivity of absorbance for acetone where more pressure is required to provide more molecules. There is less sensitivity for detection in FIG. 10 than in FIG. 11. The pressures used are much lower (50, 25, 10 mtorr) in the high finesse arrangement as the data in FIG. 11 shows compared to the pressures (200, 100, 50, 25 mtorr) used in FIG. 10 for similar absorbance plots.

Resonant Multipass Cell

Standard multipass cells, such as a Herriott cell, are single-pass multipass cells; the Herriott cell design is described by Tarsitano, Christopher G, et. al., "Multilaser Herriott cell for planetary tunable laser spectrometers", Applied Optics, Vol. 46, No. 28, 1 Oct. 2007, 6923-6935. In a Herriott cell, a light beam enters through a hole in a mirror. The light beam bounces back and forth between mirrors in the Herriott cell until the light beam leaves through the same hole in the mirror that the light beam entered the Herriott cell. A standard multipass cell would not work in the embodiments of the invention, because the output light field exiting the Herriott cell is identical to the input light field except that output light field is attenuated. Instead, in a further embodiment of the invention, a multipass cell that is resonant is required, because the feedback of the resonant system alters the light field such that the light field experiences a ring-up and ring-down. In this case, the Herriott cell must be modified to have an input coupler and an output coupler in the beam path with appropriate reflectivity such that the light is reflected back upon itself inside the cavity of the Herriott cell so that an energy buildup is created. Thus, in this further embodiment of the invention, the optical ringdown cavity comprises a multipass cell adapted to be resonant, the multipass cell having an input coupler and an output coupler positioned or located in a beam path and having a reflectivity that reflects light back upon itself inside a cavity of the multipass cell. The multipass cell that is resonant is a Herriott cell that is resonant.

The methods and systems disclosed herein provide improved systems and methods for rapid digital optical spectrum analysis of absorbance data, being particularly useful for real-time spectral monitoring of an absorbance signal, although not limited to this field. It will be appreciated by those skilled in the art in the light of this disclosure that the methods and systems disclosed herein have far-reaching application and are not linked just to the optical domain, but also to signals in other electronic systems, e.g. electronic signals or microwave/shortwave/long-wave/mobile communications among many others and use of the present methods in any such applications is use within the scope of the invention.

Thus, the systems and methods described herein and/or shown in the drawings are presented by way of example only and are not limiting as to the scope of the invention. Unless otherwise specifically stated, individual aspects and components of the signal generation and analysis methods and systems may be modified, or may have been substituted therefore known equivalents, or as yet unknown substitutes such as may be developed in the future or such as may be found to be acceptable substitutes in the future. The signal generation and analysis methods and system may also be modified for a variety of applications while remaining within the scope and spirit of the claimed invention, since the range of potential applications is great, and since it is intended that the present signal generation and analysis methods and apparatus be adaptable to many such variations.

The invention claimed is:

1. A method of generating and processing a real-time time-domain cavity ringdown spectroscopy (CRDS) signal from an absorbing species in an optical detection system having an optical ringdown cavity, said optical ringdown cavity adapted for accepting a sample of an absorbing species, said method comprising:
generating modulated light signals using a plurality of light sources having different wavelengths, the light sources being pulsed at specified pulse rates, each modulated light signal having a plurality of harmonic frequency components for a respective pulse;
simultaneously resonating said modulated light signals using the optical ringdown cavity comprising a plurality of mirrors to produce the CRDS signal, each mirror having the same or substantially the same reflectivity, the selectivity of said mirrors dependent upon said pulse rate of said modulated light signals and reflectivities of said mirrors, different beamlines being established by said modulated light signals and said mirrors interacting with the absorbing species sample; and
simultaneously demodulating using a single photodetector the CRDS signal dependent upon selected harmonics of the modulated light signals, each beamline being detected simultaneously using the single photodetector.

2. The method as claimed in claim 1, wherein:
the simultaneously demodulating comprises detecting using the single photodetector the CRDS signal output from the optical ringdown cavity; and
the method comprises estimating cavity ringdown times $\tau$ based on a ratio of harmonics and determining spectra for the absorbing species sample from the detected CRDS signal by mixing the detected CRDS signal dependent upon the wavelengths and the selected harmonics of the modulated light signals from said light sources.

3. A method of generating and processing a real-time time-domain cavity ringdown spectroscopy (CRDS) signal from an absorbing species in an optical detection system having an optical ringdown cavity, said optical ringdown cavity adapted for accepting a sample of an absorbing species, said method comprising:
generating a modulated light signal using a light source, the light source being pulsed at a specified pulse rate, the modulated light signal having a plurality of harmonic frequency components for a pulse;
resonating said modulated light signal using the optical ringdown cavity comprising a plurality of sets of mirrors to produce the CRDS signal, each set of mirrors having the same or substantially the same reflectivity, the selectivity of said sets of mirrors dependent upon said pulse rate of said modulated light signal and reflectivities of said sets of mirrors, different beamlines being established by said modulated light signal and said sets of mirrors interacting with the absorbing species sample; and
simultaneously demodulating using a single photodetector the CRDS signal dependent upon selected harmonics of the modulated light signal, each beamline being detected simultaneously using the single photodetector.

4. The method as claimed in claim 3, wherein:
the simultaneously demodulating comprises detecting using the single photodetector the CRDS signal output from the optical ringdown cavity; and
the method comprises estimating cavity ringdown times $\tau$ based on a ratio of harmonics and determining spectra for the absorbing species sample from the detected CRDS signal by mixing the detected CRDS signal dependent upon the selected harmonics of the modulated light signal from said light source.

5. A method of generating and processing a real-time time-domain cavity ringdown spectroscopy (CRDS) signal from an absorbing species in an optical detection system having an optical ringdown cavity, said optical ringdown cavity adapted for accepting a sample of an absorbing species, said method comprising:
generating modulated light signals using a plurality of light sources having different wavelengths, the light sources being pulsed at specified pulse rates, each modulated light signal having a plurality of harmonic frequency components for a respective pulse;
simultaneously resonating said modulated light signals using the optical ringdown cavity comprising a plurality of sets of mirrors to produce the CRDS signal, each set of mirrors having the same or substantially the same reflectivity, the selectivity of said sets of mirrors dependent upon the pulse rates of said modulated light signals and reflectivities of said sets of mirrors, different beamlines being established by said modulated light signals and said sets of mirrors interacting with the absorbing species sample; and
simultaneously demodulating using a single photodetector the CRDS signal dependent upon selected harmonics of the modulated light signals, each beamline being detected simultaneously using the single photodetector.

6. The method as claimed in claim 5, wherein:
the simultaneously demodulating comprises detecting using the single photodetector the CRDS signal output from the optical ringdown cavity; and
the method comprises estimating cavity ringdown times $\tau$ based on a ratio of harmonics and determining spectra for the absorbing species sample from the detected CRDS signal by mixing the detected CRDS signal dependent upon the wavelengths and the selected harmonics of the modulated light signals from said light sources.

7. The method as claimed in claim 1, wherein said different beamlines are adjusted such that the reflectivity of input and output mirrors of the plurality of mirrors of the optical ringdown cavity are different for each beamline.

8. The method as claimed in claim 2, wherein the estimating step comprises calculating a power of selected harmonics using mixers and signal sources for the selected harmonics.

9. The method as claimed in claim 2, wherein the spectra determining step comprises plotting the ring-down rate R or the reciprocal of the ring-down decay constant $1/\tau$ versus the wavelength $\lambda$ of the incident light.

10. The method as claimed in claim 2, further comprising identifying the absorbing species by comparing the determined spectra for the absorbing species sample with a library of predetermined spectra for known elements.

11. The method as claimed in claim 2, wherein the different beamlines obtained using mirrors with selected reflectivities and the use of matching pulse rate(s) of the light source(s) allows the estimating and determining steps to be optimally processed.

12. The method as claimed in claim 2, further comprising controlling, dependent upon the detected CRDS signal, at least some of the plurality of light sources, the optical ringdown cavity, or both.

13. An optical detection system for generating and processing a real-time time-domain cavity ringdown spectroscopy (CRDS) signal from an absorbing species, said system comprising:
a plurality of light sources having different wavelengths that generate modulated light signals, the light sources being pulsed at specified pulse rates, each modulated light signal having a plurality of harmonic frequency components for a respective pulse;
an optical ringdown cavity adapted for accepting a sample of an absorbing species, said optical ringdown cavity comprising a plurality of mirrors configured to resonate simultaneously said modulated light signals to produce the CRDS signal, each mirror having the same or substantially the same reflectivity, the selectivity of said plurality of mirrors dependent upon said pulse rate of said modulated light signals and reflectivities of said plurality of mirrors, different beamlines being established by said modulated light signals and said plurality of mirrors interacting with the absorbing species sample; and
a data processing module for simultaneously demodulating using a single photodetector the CRDS signal dependent upon selected harmonics of the modulated light signals, each beamline being detected simultaneously using the single photodetector.

14. The optical detection system as claimed in claim 13, further comprising:
a photodetector for detecting the CRDS signal output from the optical ringdown cavity; and
a module for estimating cavity ringdown times $\tau$ based on a ratio of harmonics and a module for determining spectra for the absorbing species sample from the detected CRDS signal by mixing the detected CRDS signal dependent upon the wavelengths and the selected harmonics of the modulated light signals from said light sources.

15. An optical detection system for generating and processing a real-time time-domain cavity ringdown spectroscopy (CRDS) signal from an absorbing species, the system comprising:
a light source that generates a modulated light signal, the light source being pulsed at a specified pulse rate, the modulated signal having a plurality of harmonic frequency components for a pulse;
an optical ringdown cavity adapted for accepting a sample of an absorbing species, said optical ringdown cavity comprising a plurality of sets of mirrors configured to resonate said modulated light signal to produce the CRDS signal, each set of mirrors having the same or substantially the same reflectivity, the selectivity of said mirrors dependent upon said pulse rate of said modulated light signal and reflectivities of said sets of mirrors, different beamlines being established by said modulated light signal and said sets of mirrors interacting with the absorbing species sample; and
a data processing module for simultaneously demodulating using a single photodetector the CRDS signal dependent upon selected harmonics of the modulated light signal, each beamline being detected simultaneously using the single photodetector.

16. The optical detection system as claimed in claim 15, further comprising:
a photodetector for detecting the CRDS signal output from the optical ringdown cavity; and
a module for estimating cavity ringdown times $\tau$ based on a ratio of harmonics and a module for determining spectra for the absorbing species sample from the detected CRDS signal by mixing the detected CRDS signal dependent upon the selected harmonics of the modulated light signal from said light source.

17. An optical detection system for generating and processing a real-time time-domain cavity ringdown spectroscopy (CRDS) signal from an absorbing species, said system comprising:
a plurality of light sources having different wavelengths that generate modulated light signals, the light sources being pulsed at specified pulse rates, each modulated signal having a plurality of harmonic frequency components for a respective pulse;
an optical ringdown cavity adapted for accepting a sample of an absorbing species, said optical ringdown cavity comprising a plurality of sets of mirrors configured to resonate simultaneously said modulated light signals to produce the CRDS signal, each set of mirrors having the same or substantially the same reflectivity, the selectivity of said mirrors dependent upon the pulse rates of said modulated light signals and reflectivities of said sets of mirrors, different beamlines being established by said modulated light signals and said sets of mirrors interacting with the absorbing species sample, each beamline being detected simultaneously using the single photodetector; and
a data processing module for simultaneously demodulating using a single photodetector the CRDS signal dependent upon selected harmonics of the modulated light signals, each beamline being detected simultaneously using the single photodetector.

18. The optical detection system as claimed in claim 17, further comprising:
a photodetector for detecting the CRDS signal output from the optical ringdown cavity; and
a module for estimating cavity ringdown times $\tau$ based on a ratio of harmonics and a module for determining spectra for the absorbing species sample from the detected CRDS signal by mixing the detected CRDS signal dependent upon the wavelengths and the selected harmonics of the modulated light signals from said light sources.

19. The optical detection system as claimed in claim 13, wherein said different beamlines are adjusted such that the reflectivity of input and output mirrors of the plurality of mirrors of the optical ringdown cavity are different for each beamline.

20. The optical detection system as claimed in claim 14, wherein the estimating module comprises a module for calculating a power of selected harmonics using mixers and signal sources for the selected harmonics.

21. The optical detection system as claimed in claim 14, wherein the spectra determining module comprises a module for plotting the ring-down rate R or the reciprocal of the ring-down decay constant $1/\tau$ versus the wavelength $\lambda$ of the incident light.

22. The optical detection system as claimed in claim 14, wherein the spectra determining module comprises a module for plotting the ring-down rate R or the reciprocal of the ring-down decay constant $1/\tau$ versus the wavelength $\lambda$ of the incident light.

23. The optical detection system as claimed in claim 14, wherein the different beamlines obtained using the plurality of mirrors with selected reflectivities and the use of matching pulse rate(s) of the light sources(s) allows the estimating and determining steps to be optimally processed.

24. The optical detection system as claimed in claim 14, further comprising a module for controlling dependent upon the detected CRDS signal, at least some of the plurality of light sources, the optical ringdown cavity, or both.

25. The method as claimed in claim 1, wherein the optical ringdown cavity comprises a multipass cell adapted to be resonant, said resonant multipass cell having an input coupler and an output coupler positioned or located in a beampath and having a reflectivity that reflects light back upon itself inside a cavity of said resonant multipass cell.

26. The method as claimed in claim 25, wherein the resonant multipass cell comprises a Herriott Cell.

27. The method as claimed in claim 3, wherein the optical ringdown cavity comprises a multipass cell adapted to be resonant, said resonant multipass cell having an input coupler and an output coupler positioned or located in a beampath and having a reflectivity that reflects light back upon itself inside a cavity of said resonant multipass cell.

28. The method as claimed in claim 27, wherein the resonant multipass cell comprises a Herriott Cell.

29. The method as claimed in claim 5, wherein the optical ringdown cavity comprises a multipass cell adapted to be resonant, said resonant multipass cell having an input coupler and an output coupler positioned or located in a beampath and having a reflectivity that reflects light back upon itself inside a cavity of said resonant multipass cell.

30. The method as claimed in claim 29, wherein the resonant multipass cell comprises a Herriott Cell.

31. The optical detection system as claimed in claim 13, wherein the optical ringdown cavity comprises a multipass cell adapted to be resonant, said resonant multipass cell having an input coupler and an output coupler positioned or located in a beampath and having a reflectivity that reflects light back upon itself inside a cavity of said resonant multipass cell.

32. The optical detection system as claimed in claim 31, wherein the resonant multipass cell comprises a Herriott Cell.

33. The optical detection system as claimed in claim 15, wherein the optical ringdown cavity comprises a multipass cell adapted to be resonant, said resonant multipass cell having an input coupler and an output coupler positioned or located in a beampath and having a reflectivity that reflects light back upon itself inside a cavity of said resonant multipass cell.

34. The optical detection system as claimed in claim 33, wherein the resonant multipass cell comprises a Herriott Cell.

35. The optical detection system as claimed in claim 17, wherein the optical ringdown cavity comprises a multipass cell adapted to be resonant, said resonant multipass cell having an input coupler and an output coupler positioned or located in a beampath and having a reflectivity that reflects light back upon itself inside a cavity of said resonant multipass cell.

36. The optical detection system as claimed in claim 35, wherein the resonant multipass cell comprises a Herriott Cell.

37. The method as claimed in claim 2, wherein said different beamlines are adjusted such that the reflectivity of input and output mirrors of the plurality of mirrors of the optical ringdown cavity are different for each beamline.

38. The method as claimed in claim 3, wherein said different beamlines are adjusted such that the reflectivity of input and output mirrors of the plurality of sets of mirrors of the optical ringdown cavity are different for each beamline.

39. The method as claimed in claim 4, wherein the estimating step comprises calculating a power of selected harmonics using mixers and signal sources for the selected harmonics.

40. The method as claimed in claim 6, wherein the estimating step comprises calculating a power of selected harmonics using mixers and signal sources for the selected harmonics.

41. The method as claimed in claim 4, wherein the spectra determining step comprises plotting the ring-down rate R or the reciprocal of the ring-down decay constant $1/\tau$ versus the wavelength $\lambda$ of the incident light.

42. The method as claimed in claim 6, wherein the spectra determining step comprises plotting the ring-down rate R or the reciprocal of the ring-down decay constant $1/\tau$ versus the wavelength $\lambda$ of the incident light.

43. The method as claimed in claim 4, further comprising identifying the absorbing species by comparing the determined spectra for the absorbing species sample with a library of predetermined spectra for known elements.

44. The method as claimed in claim 6, further comprising identifying the absorbing species by comparing the determined spectra for the absorbing species sample with a library of predetermined spectra for known elements.

45. The method as claimed in claim 4, wherein the different beamlines obtained using the plurality of sets of mirrors with selected reflectivities and the use of matching pulse rate(s) of the light source(s) allows the estimating and determining steps to be optimally processed.

46. The method as claimed in claim 6, wherein the different beamlines obtained using the plurality of sets of mirrors with selected reflectivities and the use of matching pulse rate(s) of the light source(s) allows the estimating and determining steps to be optimally processed.

47. The method as claimed in claim 4, further comprising controlling dependent upon the detected CRDS signal, the light source, the optical ringdown cavity, or both.

48. The method as claimed in claim 6, further comprising controlling dependent upon the detected CRDS signal, at least some of the plurality of light sources, the optical ringdown cavity, or both.

49. The optical detection system as claimed in claim 15, wherein said different beamlines are adjusted such that the reflectivity of input and output mirrors of the plurality of sets of mirrors of the optical ringdown cavity are different for each beamline.

50. The optical detection system as claimed in claim 17, wherein said different beamlines are adjusted such that the reflectivity of input and output mirrors of the plurality of sets of mirrors of the optical ringdown cavity are different for each beamline.

51. The optical detection system as claimed in claim 16, wherein the estimating module comprises a module for calculating a power of selected harmonics using mixers and signal sources for the selected harmonics.

52. The optical detection system as claimed in claim 18, wherein the estimating module comprises a module for calculating a power of selected harmonics using mixers and signal sources for the selected harmonics.

53. The optical detection system as claimed in claim 16, wherein the spectra determining module comprises a module for plotting the ring-down rate R or the reciprocal of the ring-down decay constant $1/\tau$ versus the wavelength $\lambda$ of the incident light.

54. The optical detection system as claimed in claim 18, wherein the spectra determining module comprises a module for plotting the ring-down rate R or the reciprocal of the ring-down decay constant $1/\tau$ versus the wavelength $\lambda$ of the incident light.

55. The optical detection system as claimed in claim 16, wherein the spectra determining module comprises a module for plotting the ring-down rate R or the reciprocal of the ring-down decay constant $1/\tau$ versus the wavelength $\lambda$ of the incident light.

56. The optical detection system as claimed in claim 18, wherein the spectra determining module comprises a module for plotting the ring-down rate R or the reciprocal of the ring-down decay constant $1/\tau$ versus the wavelength $\lambda$ of the incident light.

57. The optical detection system as claimed in claim 16, wherein the different beamlines obtained using the plurality of sets of mirrors with selected reflectivities and the use of matching pulse rate(s) of the light sources(s) allows the estimating and determining steps to be optimally processed.

58. The optical detection system as claimed in claim 18, wherein the different beamlines obtained using the plurality of sets of mirrors with selected reflectivities and the use of matching pulse rate(s) of the light sources(s) allows the estimating and determining steps to be optimally processed.

59. The optical detection system as claimed in claim 16, further comprising a module for controlling dependent upon the detected CRDS signal, the light source, the optical ring-down cavity, or both.

60. The optical detection system as claimed in claim 18, further comprising a module for controlling dependent upon the detected CRDS signal, at least some of the plurality of light sources, the optical ringdown cavity, or both.

\* \* \* \* \*